United States Patent
Hansson

(10) Patent No.: US 9,642,657 B2
(45) Date of Patent: May 9, 2017

(54) DEVICE FOR FIXATION OF BONE FRAGMENTS AT BONE FRACTURES

(71) Applicant: Swemac Innovation AB, Linkoping (SE)

(72) Inventor: Henrik Hansson, Vreta Kloster (SE)

(73) Assignee: Swemac Innovation AB (SE)

( * ) Notice: Subject to any disclaimer, the term of this patent is extended or adjusted under 35 U.S.C. 154(b) by 15 days.

(21) Appl. No.: 14/582,231

(22) Filed: Dec. 24, 2014

(65) Prior Publication Data

US 2015/0201980 A1    Jul. 23, 2015

(30) Foreign Application Priority Data

Jan. 4, 2014   (JP) .................................. 2014-000009

(51) Int. Cl.
*A61B 17/74*    (2006.01)
*A61B 17/84*    (2006.01)
*A61B 17/80*    (2006.01)

(52) U.S. Cl.
CPC ........ *A61B 17/746* (2013.01); *A61B 17/8057* (2013.01); *A61B 17/844* (2013.01)

(58) Field of Classification Search
CPC .. A61B 17/746; A61B 17/844; A61B 17/8057
See application file for complete search history.

(56) References Cited

U.S. PATENT DOCUMENTS 2,631,584 A * 3/1953 Purificato ............ A61B 17/746
111/7.1
3,530,854 A * 9/1970 Kearney .............. A61B 17/746
606/67

(Continued)

FOREIGN PATENT DOCUMENTS

JP        2012125547 A  *  7/2012

OTHER PUBLICATIONS

Schreiber Translations, Inc., English Translation of JP2012/125547, Aug. 2016, Henrik Hansen, 1-25.*

*Primary Examiner* — Ellen C Hammond
(74) *Attorney, Agent, or Firm* — Tarolli, Sundheim, Covell & Tummino LLP

(57) ABSTRACT

The present invention relates to a device for fixation of bone fragments at bone fractures. The device comprises at least two fixation means (1) and a securing plate (17). The securing plate (17) has threaded holes (19). The fixation means consist of bone nails (1) which each comprises a sleeve (5) with a displaceable pin (7) inside the sleeve. A forward portion (9) of the (7) pin defines a first fixing portion for fixing the bone nail (1) in an inner bone fragment (3). A threaded rear end portion (18) of the sleeve (5) defines a second fixing portion for locking the bone nail (1) to the securing plate (17). The sleeve (5) has a middle portion (32) along which the outer bone fragment (2) can slide inwards towards the inner bone fragment (3). The thread of each threaded hole (19) in the securing plate (17) is configured such that after screwing of the threaded rear end portion (18) of the sleeve (5) into the threaded hole until it reaches a surface in the hole against which said threaded rear end portion can abut, a side aperture for the pin (7) in the sleeve is oriented in a predetermined direction in the inner bone fragment (3).

14 Claims, 3 Drawing Sheets

(56) References Cited

U.S. PATENT DOCUMENTS

| | | | | |
|---|---|---|---|---|
| 4,498,468 | A * | 2/1985 | Hansson | A61B 17/742 433/173 |
| 7,850,699 | B2 * | 12/2010 | Hansson | A61B 17/92 606/104 |
| 8,118,846 | B2 * | 2/2012 | Leither | A61B 17/8057 606/280 |
| 9,259,253 | B2 * | 2/2016 | Kay | A61B 17/8057 |
| 2006/0173459 | A1 * | 8/2006 | Kay | A61B 17/8061 606/71 |
| 2007/0073298 | A1 * | 3/2007 | Beutter | A61B 17/80 606/301 |
| 2015/0289915 | A1 * | 10/2015 | Hansson | A61B 17/844 606/328 |

* cited by examiner

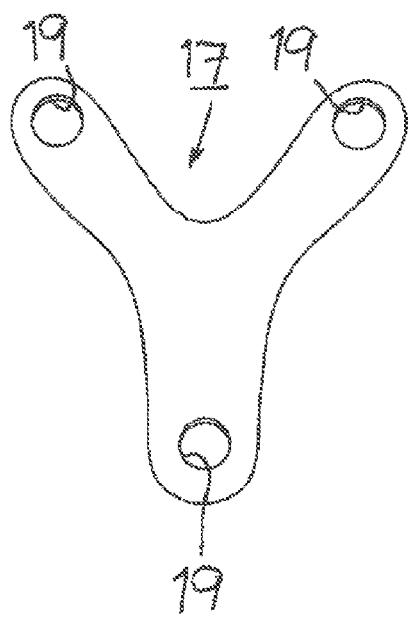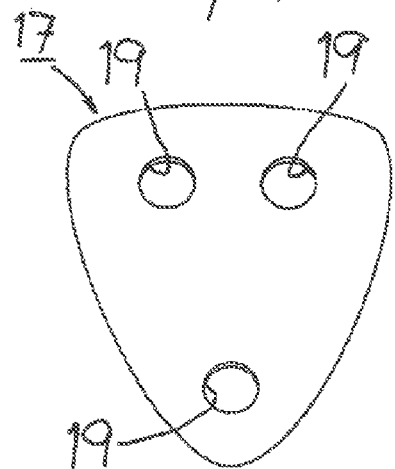

DEVICE FOR FIXATION OF BONE FRAGMENTS AT BONE FRACTURES

BACKGROUND OF THE INVENTION

The present invention relates to a device for fixation of bone fragments at bone fractures. The device comprises at least two fixation means and a securing plate.

After a bone fracture such as a femur neck fracture, the bone fragments at the fracture need fixing. This is currently done by using suitable fixation means, e.g. bone nails or bone screws.

After the completion of surgery, even as early as when the effects of the anaesthesia have passed and the patient is still confined to bed, but above all when the patient is beginning to be up and walk and stand on the leg, the fixed bone fragments and the fixation means are subject to large forces, particularly to rotational forces downwards and rearwards.

The fixation means alone are often insufficient to counteract these rotational forces and the bone fragments have to be used to help to lock the fracture. If this is not done and the bone fragments are caused to rotate relative to one another by said forces, the result will be shifting of the angular positions of the fixation means to such an extent that they risk substantially crossing one another, thereby keeping the fracture parted and preventing healing.

When fixation means in the form of bone nails comprising a sleeve and a displaceable pin in the sleeve are used, it is very difficult to verify that these fixation means are correctly located and correctly oriented in the inner bone fragment, e.g. the head of femur.

BRIEF SUMMARY OF INVENTION

An important object of the present invention is accordingly to prevent or counteract rotational forces and therefore configure the device in such a way that the fixation means are not allowed to rotate and cross one another.

Another important object of the present invention is to see to that fixation moans in the form of bone nails comprising a sleeve and a pin which is displaceably located in the sleeve, are correctly located and oriented in the inner bone fragment, e.g. the head of femur.

To this end, according to the invention, the securing plate of the device is configured with a threaded hole for each fixation means. Fixation means forming part of the device, each in the form of a bone nail which comprises a sleeve and, disposed therein, a pin arranged for movement in the sleeve so that at least a forward portion of the pin can be driven outwards through at least one side aperture in the sleeve, are also provided. The forward portion of the pin constitutes a first fixing portion in the form of at least one hook which engages in an inner bone fragment for fixing the bone nail therein. The rear end portion of the sleeve is threaded and defines a second fixing portion for locking the bone nail to the securing plate. The securing plate is disposed on the outside of an outer bone fragment without fixed connection therewith such that movement of the outer bone fragment relative to the securing plate is allowed and change of the angular position of the bone nails relative to the securing plate and relative to one another is prevented. A middle portion of the sleeve is situated between the side aperture in the sleeve and the second fixing portion thereof and runs through the outer bone fragment. This middle portion is configured such that the outer bone fragment during secondary compression can slide inwards therealong away from the securing plate and towards the inner bone fragment in which the bone nail is fixed. Finally, the thread of each threaded hole in the securing plate is configured such that after screwing of the threaded rear end portion of the sleeve info the threaded hole until the sleeve reaches a surface in the hole against which said threaded rear end portion can abut the side aperture in the sleeve is oriented in a predetermined direction in the inner bone fragment.

The result of the fixation means in the form of bone nails being thus fixed to the inner bone fragment and to the securing plate while the outer bone fragment can move towards the inner bone fragment and, in so doing, be guided by the bone nail, is that the bone fragments are kept fixed but (secondary) compression of the bone fragments is nevertheless allowed, the device and the bone fragments thus being able to absorb the aforesaid rotational forces and control them so that no re-dislocation occurs and the bone is allowed to heal from inner parts thereof and outwards. By the secondary compression such that the outer bone fragment moves towards the inner bone fragment, many possible spaces between the bone fragments due to the fracture and/or due to necrosis of the bone material at the fracture can be eliminated, which otherwise can lead to fatigue failures of the bone nails or break down of the bone. The fixing of the bone nails in the inner bone fragment by correct location and orientation of the first fixing portions thereof, and the locking of the bone nails to the securing plate also reduce the risk of loosening of bone nails of the type defined above.

Other objects and advantages of the invention will be apparent to one skilled in the art who examines the attached drawings and the following detailed description of a preferred embodiment of the device according to the invention.

BRIEF DESCRIPTION OF THE DRAWINGS

FIGS. 3 and 4 depict very schematic front views of two different alternative versions of the securing plate.

DETAILED DESCRIPTION OF A PREFERRED EMBODIMENT OF THE INVENTION

Figure 1:
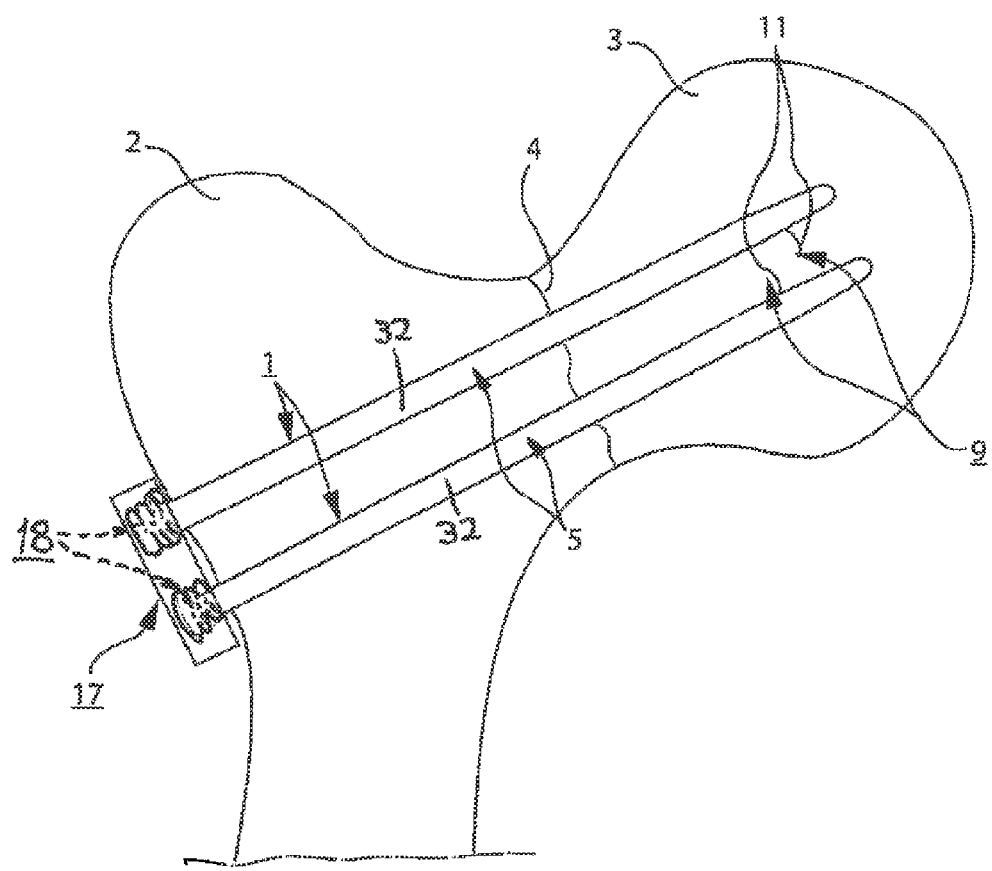
FIG. 1 is a schematic longitudinal section through upper portions of a femur with a fracture at the neck of the femur and provided with a device according to the present invention, of which a securing plate and two fixation means are illustrated.

As already mentioned, FIG. 1 depicts upper portions of a femur with a femur neck fracture, and an outer bone fragment 2 and an inner bone fragment 3 on their respective sides of the fracture 4. If should be noticed however, that the type of bone fracture at which bone fragments have to be fixed, may vary. A securing plate 17 which forms part of the device according to the present invention for fixation means in the form of bone nails, in the version depicted two substantially parallel bone nails 1 for fixing the bone fragments 2, 3, is disposed on the outside of the outer bone fragment 2. The securing plate 17 is so arranged that it allows movement of the outer bone fragment 2 relative to it, i.e. it is not fixedly connected to the outer bone fragment nor arranged in some other way whereby it would have moved with the latter upon (secondary) compression of the bone fragments 2, 3. The securing plate 17 is configured with threaded holes 19. The number of holes 19 corresponds to the number of bone nails 1, i.e. at least two as illustrated in FIG. 1, or three as according to FIG. 3 and 4, or four or more if desired. It should be noticed however, that the embodiments of the securing plate 17 illustrated in FIGS. 3 and 4 are very schematic, intended only to show alternative outer shapes of the plate. The thickness of the securing plates 17 must be sufficient for being able to configure the holes 19 with threads.

As indicated, although FIG. 1 depicts two substantially parallel fixation means in the form of bone nails 1, the number of fixation means may vary. Each bone nail 1 comprises a cylindrical sleeve 5 with a longitudinal space 6 which is open rearwards for insertion of a pin 7 which is preferably cylindrical at least rearwards, with an outside diameter at least partly adapted to the inside diameter of tie sleeve. This pin 7 is movable in the longitudinal direction of the sleeve 5 and has a rear portion and at least one forward portion 9 which extends forward from the rear portion. The forward portion 9 has at its front end a curved tip 11.

Forward portions of the sleeve 5 have at least one aperture 13 on a side of the sleeve. The forward portion 9 of the pin 7 can be driven through the side aperture 13 outwards from the sleeve 5 by the pin being driven forwards relative to the sleeve. This driving of the pin 7 forwards relative to the sleeve 5 may be effected by using a suitable type of driving tool (not depicted).

The space of the sleeve 5 ends forwards with at least one guide surface 15 directed obliquely forwards/outwards relative to a centreline CL which runs in a longitudinal direction through the space 6 of the sleeve and thus constitutes the longitudinal axis of the bone nail.

In a state of readiness (not depicted) in which the pin 7 is inserted in the sleeve 5, the tip 11 of the pin abuts against or is situated close to the guide surface 15.

A method for fixation of a fracture at the neck of a femur, may start by drilling a guide wire with a diameter of e.g. about 2,4 mm through the outer bone fragment 2 and into the inner bone fragment 3 under radioscopy and with guidance by a guide sleeve with an inside diameter of e.g. about 2.5 mm. The guide wire is configured to guide a drill for drilling a hole for the bone nail 5 in the bone fragments 2, 3. The guide sleeve for the guide wire is applied in the securing plate 17, by preferably being screwed firmly into one of the threaded holes 19 running through the plate, and having for the purpose an externally threaded forward end portion. This externally threaded forward end portion does of course have an outside diameter corresponding to the diameter of the threaded hole 19 in the securing plate 17, i.e. preferably about 9-10 mm.

After the removal of the guide sleeve for the guide wire, a second guide sleeve, with an inside diameter of e.g. about 6.5 mm and an externally threaded forward portion with the same outside diameter as the first guide sleeve, may be applied in, i.e. screwed into, the threaded hole 19 in the securing plate 17. This guide sleeve is configured to guide a drill, which has running through it a duct for the wire guide, for drilling the hole for the sleeve 5 of the bone nail 1 in the bone fragments 2, 3. When the second guide sleeve has been attached to the securing plate 17, a gauge rod may be inserted at the rear of this guide sleeve and through said sleeve towards the bone 2, 3, The gauge rod can be used in a conventional manner to indicate how far the drilling should go or how long the bone nail 1 should be for optimum function.

The hole for the sleeve 5 of the bone nail 1 can now be drilled. Accordingly, the drill provided with the duct may be introduced through the guide sleeve towards the outer bone fragment 2 and the drilling of the hole for the sleeve 5 of the bone nail 1 is commenced, using a suitable drive device. The drill may have an outside diameter of preferably about 6.5 mm and fits exactly in the guide sleeve. The drill is guided by the guide sleeve to a correct position against the outer bone fragment 2 and thereafter by the guide wire through the outer bone fragment 2 and past the fracture 4 info the inner bone fragment 3. Monitoring that the hole for the sleeve 5 of the bone nail 1 is of a correct length is carried out e.g. at the rear of the guide sleeve, where the drill or the drive device bears suitable markings.

After any necessary adjustment of the securing plate 17 sideways, a further second guide sleeve may now be applied in a second threaded hole 19 running through the plate. Alternatively, a guide sleeve for a guide wire may be applied first and the same procedure as before, with the same parts as above, may be carried out. With advantage, guide sleeves of desired kinds may already from the outset be applied in the respective threaded holes 19 in the securing plate 17 to give the surgeon a better grasp for correct control of the guide wire and the respective drills. The guide sleeve may be configured to guide a drill without a duct for the guide wire but with a conical tip. This solid drill may be driven in to a desired position for the sleeve 5 of the bone nail 1 by means of the drive device. The correct length is read with advantage at the rear of the guide sleeve, where the drill or the drive device bears suitable markings. The drill and the guide sleeve for if are removed, leaving a hole for the sleeve 5 of the bone nail 1 in the bone fragments 2, 3.

Figure 2:
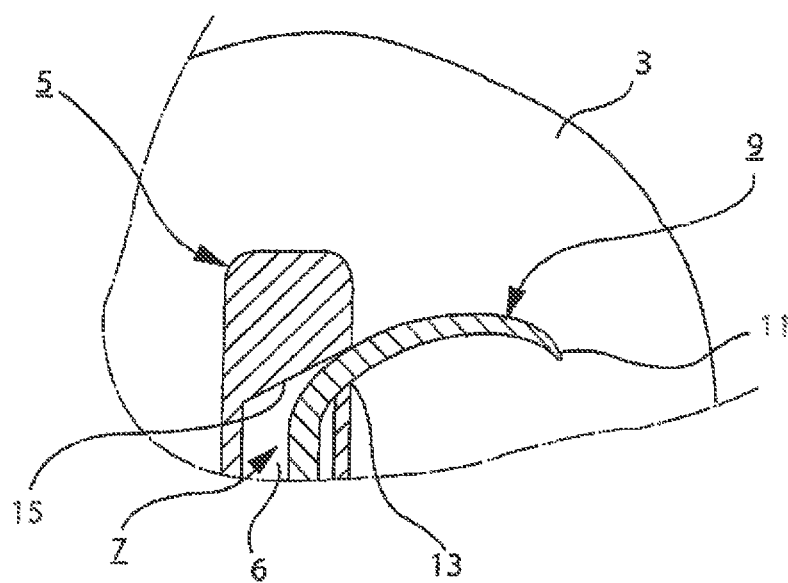
FIG. 2 is a schematic longitudinal section through portions of the head of the femur and forward portions of a fixation means.

In the version depicted, when holes for the respective bone nail 1 have been drilled through the outer bone fragment 2 and into the inner bone fragment 3 at the femur neck fracture 4 and the bone nail have been introduced into the holes, the pin 7 is driven outwards from the sleeve 5. During the driving of the pin 7 forwards relative to the sleeve 5, the guide surface 15 will guide the forward portion 9 of the pin outwards through the side aperture 13, said forward portion forming a hook which engages in the inner bone fragment 3 (see FIG. 2).

This hook 9 may be referred to as the first fixing portion of the bone nail 1.

A rear end portion 18 of the sleeve is configured with a thread fitting into the threaded holes 19 in the securing plate 4. This threaded rear end portion 18 of the sleeve 5 may be referred to as the second fixing portion of the bone nail 1.

The thread of each threaded hole 19 in the securing plate 17 is configured such that after screwing of the threaded rear end portion 18 of the sleeve 5 into the threaded hole until said threaded rear end portion reaches a surface in the hole against which said threaded rear end portion can abut, the side aperture 13 in the sleeve is oriented in a predetermined direction in the inner bone fragment 3. As the density in the inner bone fragment 3 is greatest at its centre, it is of advantage if the respective bone nail 1 is applied in such a way that, after the driving, the forward portion 9 of the pin 7 is caused to engage in the central portions of the inner bone fragment, i.e. that the side aperture 13 in the sleeve 6 is oriented such that if faces the central portions of the inner bone fragment after the threaded rear end portion of the sleeve has been screwed into the threaded hole 9 in the securing plate until said threaded rear end portion has reached the surface in said hole against which said threaded rear end portion can abut. This is achieved by configuring the thread of each threaded hole 19 in the securing plate 17 to allow that, e.g. by configuring said thread such that it begins at a point in the threaded hole 19 at which when the threaded rear end portion 18 of the sleeve 5 is brought to mesh therewith, the side aperture 13 will be oriented such that it faces the central portions of the inner bone fragment when said threaded rear end portion reaches the bottom of said threaded hole. The fact that the forward portion 9 of the pin 7 in the respective bone nail 1 points towards the centre of the inner bone fragment 3 means not only that the bone nails have a better grip in this inner bone fragment but also that the risk of rotation and other movements of the bone nails is counteracted.

Thus, the device according to the present invention provides for a stable connection between the securing plate 17 and the bone nails 1 which prevents the bone nails from changing their angular position relative to the plate and relative to one another in such a way that the bone nails would have crossed one another. There is also optimum fixation of the bone fragments 2, 3 by means of the bone nails 1.

However, the bone nails 1 are also configured, as a result of a smooth middle portion 32 thereof, to allow the. bone fragments 2, 3 to be compressed so that the outer bone fragment 2 can slide inwards away from the securing plate 17 and towards the inner bone fragment 3 into which the bone nails are firmly fixed. On such occasions, the securing plate 17 will, through being locked to the bone nails 1 move away from its abutment against the outer bone fragment 2 or, in other words, the securing plate will relieve its engagement with the outer bone fragment and an intermediate space between the securing plate and the outer bone fragment might even be formed, but without affecting the strength of the connection and without any impairment of function.

FIGS. 3 and 4 depict alternative versions of the securing plate 17. The securing plate 17 has in these versions three threaded holes 19 for bone nails. The threaded holes 19 are arranged in a triangular fashion, i.e. each threaded hole is located at a point defining an angle of an imaginary triangle on the securing plate 17. For providing threaded holes 19 of sufficient length for stable and effective engagement therein by the threaded rear end portions 18 of the sleeves 5 of the bone nails, the securing plates 17 need to be somewhat thicker than illustrated and said holes need to be provided with the surface against which said threaded rear end portions can abut. This abutment surface may be configured e.g. as a peripheral flange in each threaded hole 19 or as any other restriction of said hole, allowing passage of the entire bone nail 1 except for the threaded rear end portion 18 of the sleeve 5.

In all the versions depicted, the threaded holes 19 for the bone nails run substantially parallel with one another so that the bone nails 1 will likewise run substantially parallel with one another. Parallel running of the bone nails facilitates in particular the sliding movement of the outer bone fragment 2 along the bone nails 1 (along the middle portion 32 thereof) for particularly secondary compression of the bone fragments.

The securing plate 17 according to the present invention may be used not only for femur neck (collum femoris) fractures but also for, for example, upper arm (humerus) fractures.

Since during operations for fixation of bone fragments at bone fractures it is important that the bone nails 1 assume exactly predetermined positions relative to the bone fragments 2, 3 and to one another, it is of advantage that the device according to the invention also allows the application of guide sleeves for guidance of drills for drilling holes for the bone nails in the bone fragments, and/or guide sleeves for guidance of guide wires for said drills, in the same holes 19 in the securing plate 17 as are intended for the bone nails. This means that surgical staff need no longer keep count of an unnecessarily large number of different items for performing an operation, operating time becomes shorter and risks and complications for patients are reduced.

It will be obvious to one skilled in the art that the device according to the present invention can be modified and altered within the scope of the claims set out below without departing from the idea and objects of the invention. Thus, as indicated above, the securing plate 17 may be used for guide sleeves for guide wires and thereafter for guide sleeves for drills or, for example, immediately for guide sleeves for drills. The securing plate 17 may of course also be used only for guide sleeves for guide wires, followed by drill guidance solely by guide wire, without special guide sleeves for drills. The size and choice of material of the constituent items of an operating set may vary as necessary and desired.

The invention claimed is:

1. A device for fixation of bone fragments at bone fractures,
  wherein the device comprises at least two fixation means and a securing plate,
  wherein the securing plate is configured with a threaded hole for each fixation means,
  wherein each fixation means is a bone nail which comprises a sleeve and, disposed therein, a pin arranged for movement in the sleeve so that at least a forward portion of the pin can be driven outwards through at least one side aperture in the sleeve,
  wherein the forward portion of the pin constitutes a first fixing portion in the form of at least one hook which is configured to engages in an inner bone fragment for fixing the bone nail therein,
  wherein a rear end portion of the sleeve is threaded and defines a second fixing portion for locking the bone nail to the securing plate which is configured to be disposed on the outside of an outer bone fragment without fixed connection therewith such that movement of the outer bone fragment relative to the securing plate is allowed and such that change of the angular position of the bone nails relative to the securing plate and relative to one another is prevented,
  wherein a middle portion of the sleeve is situated between the side aperture in the sleeve and the second fixing portion thereof and is configured to run through the outer bone fragment, said middle portion being configured such that the outer bone fragment during secondary compression can slide inwards therealong away from the securing plate and towards the inner bone fragment in which the bone nail is fixed, and
  wherein the thread of each threaded hole in the securing plate is configured such that after screwing of the threaded rear end portion of the sleeve into the threaded hole until the said threaded rear end portion reaches a surface in the hole against which said threaded rear end portion can abut to prevent further screwing of the rear end portion into the threaded hole, the side apertures in the sleeves all being configured to face a central portion of the inner bone fragment when said threaded rear end portions abut the surfaces in the holes.

2. A device according to claim 1, wherein the thread of each threaded hole in the securing plate is configured such that after screwing of the threaded rear end portion of the sleeve into the threaded hole until said threaded rear end portion reaches the surface in the hole against which said threaded rear end portion can abut, the side apertures in the sleeve all being configured to face an axis extending along a center of the inner bone fragment.

3. A device according to claim 1, wherein the securing plate is configured with three threaded holes which are arranged in a triangular fashion.

4. A device according to claim 1, wherein the apertures in the sleeves being configured to face directions that intersect each other within the inner bone fragment.

5. A device according to claim 1, wherein the apertures in the sleeves face directions that intersect each other at an axis extending parallel to the sleeves and through the securing plate.

6. A device according to claim 1, wherein the axis is equidistant from each of the sleeves.

7. A device for fixation of bone fragments at bone fractures comprising:
- at least two bone nails, each including:
  - a sleeve having a threaded read end portion, at least one side aperture, and a middle portion positioned between the rear end portion and the at least one side aperture; and
  - a pin having at least one hook and being positioned within the sleeve and arranged for movement therein, the at least one hook being configured to be driven outwards through the at least one side aperture in the sleeve into engagement with an inner bone fragment for fixing the bone nail therein; and
- a securing plate having at least two threaded holes for receiving the threaded rear end portions of the sleeves and configured to be disposed on the outside of an outer bone fragment without fixed connections therewith to allow for movement of the outer bone fragment relative to the securing plate,
- the rear end portions of the sleeves locking the bone nails to the securing plate in a manner that prevents angular movement of the bone nails relative to the securing plate and relative movement between the bone nails, the thread of each threaded hole in the securing plate being configured such that after screwing the rear end portions of the sleeves into the holes until the threaded rear end portions abut surfaces in the holes to prevent further screwing of the rear end portion into the threaded hole, the side apertures in the sleeves face directions that intersect each other while the rear end portions abut the surfaces,
- the middle portion being configured to extend through the outer bone fragment such that the outer bone fragment during secondary compression can slide inwards therealong away from the securing plate and towards the inner bone fragment in which the bone nails are fixed.

8. A device according to claim 7, wherein the apertures in the sleeves being configured to face directions that intersect each other within the inner bone fragment.

9. A device according to claim 7, wherein the apertures in the sleeves face directions that intersect each other at an axis extending parallel to the sleeves and through the securing plate.

10. A device according to claim 9, wherein the axis equidistant from each of the sleeves.

11. A device according to claim 7, wherein the apertures in the sleeves all are configured to face a central portion of the inner bone fragment.

12. A device according to claim 11, wherein the apertures in the sleeves all are configured to face and axis extending along a center of the inner bone fragment.

13. A device according to claim 1, wherein the surface in the hole is a bottom surface.

14. a device according to claim 7, wherein the surface in the holes are bottom surfaces.

* * * * *

UNITED STATES PATENT AND TRADEMARK OFFICE
CERTIFICATE OF CORRECTION

PATENT NO. : 9,642,657 B2
APPLICATION NO. : 14/582231
DATED : May 9, 2017
INVENTOR(S) : Henrik Hansson It is certified that error appears in the above-identified patent and that said Letters Patent is hereby corrected as shown below:

In the Claims

Column 6, Line 31 reads "engages" should read --engage--

Column 6, Line 53 reads "the said" should read --said--

Column 6, Line 66 reads "sleeve" should read --sleeves--

Column 7, Line 16 reads "read" should read --rear--

Column 7, Line 29 reads "connections" should read --connection--

Column 8, Line 23 reads "equidistant" should read --is equidistant--

Column 8, Line 28 reads "and" should read --an--

Column 8, Line 32 reads "surface" should read --surfaces--

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*